US010591442B2

(12) United States Patent
Kawabata et al.

(10) Patent No.: US 10,591,442 B2
(45) Date of Patent: Mar. 17, 2020

(54) RAIL CHECK DEVICE AND RAIL CHECK SYSTEM

(71) Applicant: HITACHI HIGH-TECHNOLOGIES CORPORATION, Tokyo (JP)

(72) Inventors: Ryuzo Kawabata, Tokyo (JP); Akihiko Kandori, Tokyo (JP); Noritake Shizawa, Saitama (JP); Kenji Yamamoto, Saitama (JP); Hiroyuki Kanda, Saitama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 37 days.

(21) Appl. No.: 15/740,020

(22) PCT Filed: Mar. 11, 2016

(86) PCT No.: PCT/JP2016/057801
§ 371 (c)(1),
(2) Date: Dec. 27, 2017

(87) PCT Pub. No.: WO2017/006589
PCT Pub. Date: Jan. 12, 2017

(65) Prior Publication Data
US 2018/0172639 A1 Jun. 21, 2018

(30) Foreign Application Priority Data
Jul. 9, 2015 (JP) .................................. 2015-137823

(51) Int. Cl.
G01N 27/90 (2006.01)
G01N 27/83 (2006.01)
(Continued)

(52) U.S. Cl.
CPC ............. *G01N 27/904* (2013.01); *B61K 9/10* (2013.01); *B61L 23/044* (2013.01); *G01N 27/83* (2013.01);
(Continued)

(58) Field of Classification Search
CPC .. G01N 27/904; G01N 27/9033; G01N 27/83; G01N 27/9053; G01N 27/902; B61K 9/10; B61L 23/044
(Continued)

(56) References Cited

U.S. PATENT DOCUMENTS 2,203,256 A * 6/1940 Drake ...................... B61K 9/10
324/241
2,602,840 A * 7/1952 McKee .............. G01N 27/9033
335/297
(Continued)

FOREIGN PATENT DOCUMENTS

EP 2 282 199 A1 2/2011
JP 63-235854 A 9/1988
(Continued)

OTHER PUBLICATIONS

Gaydecki, Patrick, et al. "Inductive and magnetic field inspection systems for rebar visualization and corrosion estimation in reinforced and pre-stressed concrete." Nondestructive Testing and Evaluation  22.4 (2007): 255-298. (Year: 2007).*
(Continued)

Primary Examiner — Christopher P McAndrew
(74) Attorney, Agent, or Firm — Mattingly & Malur, PC

(57) ABSTRACT

The present invention addresses the problem of checking defects of a rail for a vehicle with a high SN ratio. A detection device (2) for generating check data related to the defects of a railway rail RR (rail for a vehicle) is provided with an oscillating coil C1 (211) and an oscillating coil C2
(Continued)

(211) that are disposed on the surface opposite the railway rail RR and generate AC magnetic fields whose directions are opposite to each other, and a receiving coil (212) that is positioned between or in the vicinity the oscillation coils and that outputs a magnetic field waveform based on the magnetic fields received from the oscillating coils as the check data.

12 Claims, 12 Drawing Sheets

(51) Int. Cl.
  *B61K 9/10* (2006.01)
  *B61L 23/04* (2006.01)
(52) U.S. Cl.
  CPC ....... *G01N 27/9033* (2013.01); *G01N 27/902* (2013.01); *G01N 27/9053* (2013.01)
(58) Field of Classification Search
  USPC .......................................................... 324/217
  See application file for complete search history.

(56) References Cited

U.S. PATENT DOCUMENTS

| | | | | | |
|---|---|---|---|---|---|
| 2,622,131 | A | * | 12/1952 | McKee | B60F 1/04 324/217 |
| 2,671,197 | A | * | 3/1954 | Barnes | B61K 9/10 361/147 |
| 2,682,442 | A | * | 6/1954 | Keaton | B61K 9/10 346/33 R |
| 2,766,424 | A | * | 10/1956 | McKee | B61K 9/10 324/217 |
| 2,869,073 | A | * | 1/1959 | McKee | G01N 27/904 324/217 |
| 3,271,662 | A | * | 9/1966 | Quittner | G01N 27/904 324/233 |
| 5,623,244 | A | * | 4/1997 | Cooper | B61L 23/041 246/166 |
| 5,786,750 | A | * | 7/1998 | Cooper | B61L 23/044 246/121 |
| 2002/0033049 | A1 | * | 3/2002 | Amini | B61K 9/10 73/636 |
| 2005/0001612 | A1 | * | 1/2005 | Buttle | G01N 3/32 324/233 |
| 2008/0315871 | A1 | * | 12/2008 | Lepage | G01N 27/9013 324/242 |
| 2011/0004452 | A1 | * | 1/2011 | Korukonda | G01N 27/904 703/2 |
| 2011/0163741 | A1 | | 7/2011 | Suzuma et al. | |
| 2013/0024135 | A1 | | 1/2013 | Blum | |
| 2015/0183448 | A1 | * | 7/2015 | Cooper | B61L 3/10 246/34 R |

FOREIGN PATENT DOCUMENTS

| | | |
|---|---|---|
| JP | 08-101168 A | 4/1996 |
| JP | 2001-108659 A | 4/2001 |
| JP | 2003-050234 A | 2/2003 |
| JP | 2003-270214 A | 9/2003 |
| JP | 2004-279055 A | 10/2004 |
| JP | 2004-279372 A | 10/2004 |
| JP | 2006-220526 A | 8/2006 |
| JP | 2013-185951 A | 9/2013 |
| JP | 2014-044151 A | 3/2014 |
| JP | 2014-66688 A | 4/2014 |
| JP | 2014-102197 A | 6/2014 |
| WO | 2013-024858 A1 | 3/2015 |

OTHER PUBLICATIONS

Maiseri, H., D. MacLauchlan, and George A. Alers. "Application of EMATs to In-Place Inspection of Railroad Rails." (1981). (Year: 1981).*

Gaydecki, P., Fernandes, B., Quek, S., Benitez, D., Miller, G. and Zaid, M., 2007. Inductive and magnetic field inspection systems for rebar visualization and corrosion estimation in reinforced and pre-stressed concrete. Nondestructive Testing and Evaluation, 22(4), pp. 255-298. (Year: 2007).*

Maiseri, H., MacLauchlan, D. and Alers, G.A., 1981. Application of EMATs to In-Place Inspection of Railroad Rails. (Year: 1981).*

Maiseri, H., MacLauchlan, D. and Alers, G.A., 1981. Application of EMATs to In-Place Inspection of Railroad Rails. (Year: 1981) ( Year: 1981).*

International Search Report of PCT/JP2016/057801 dated May 17, 2016.

Extended European Search Report received in corresponding European Application No. 16821060.7 dated Dec. 7, 2018.

* cited by examiner

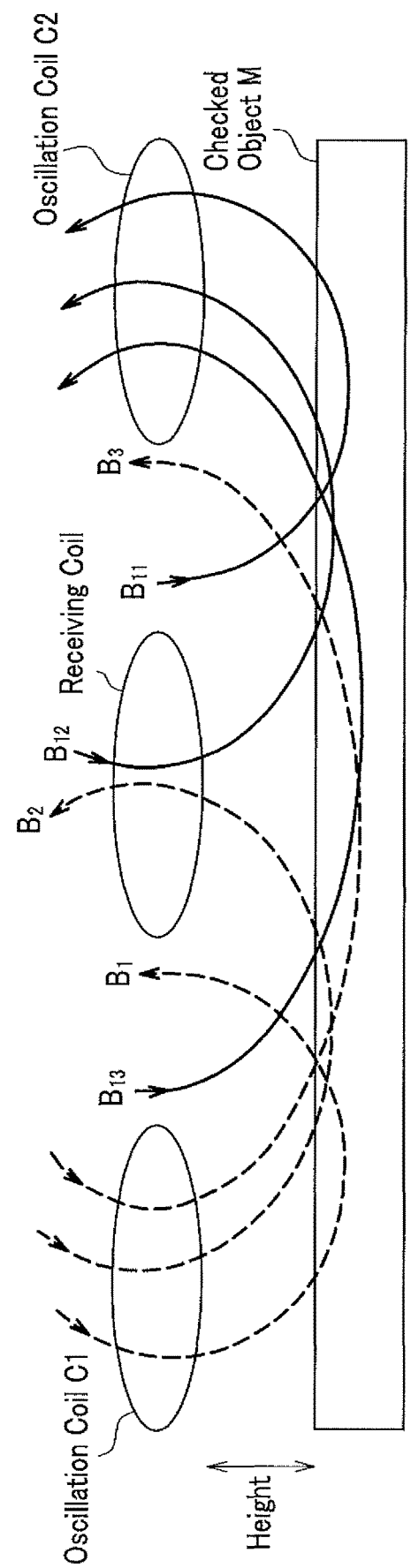

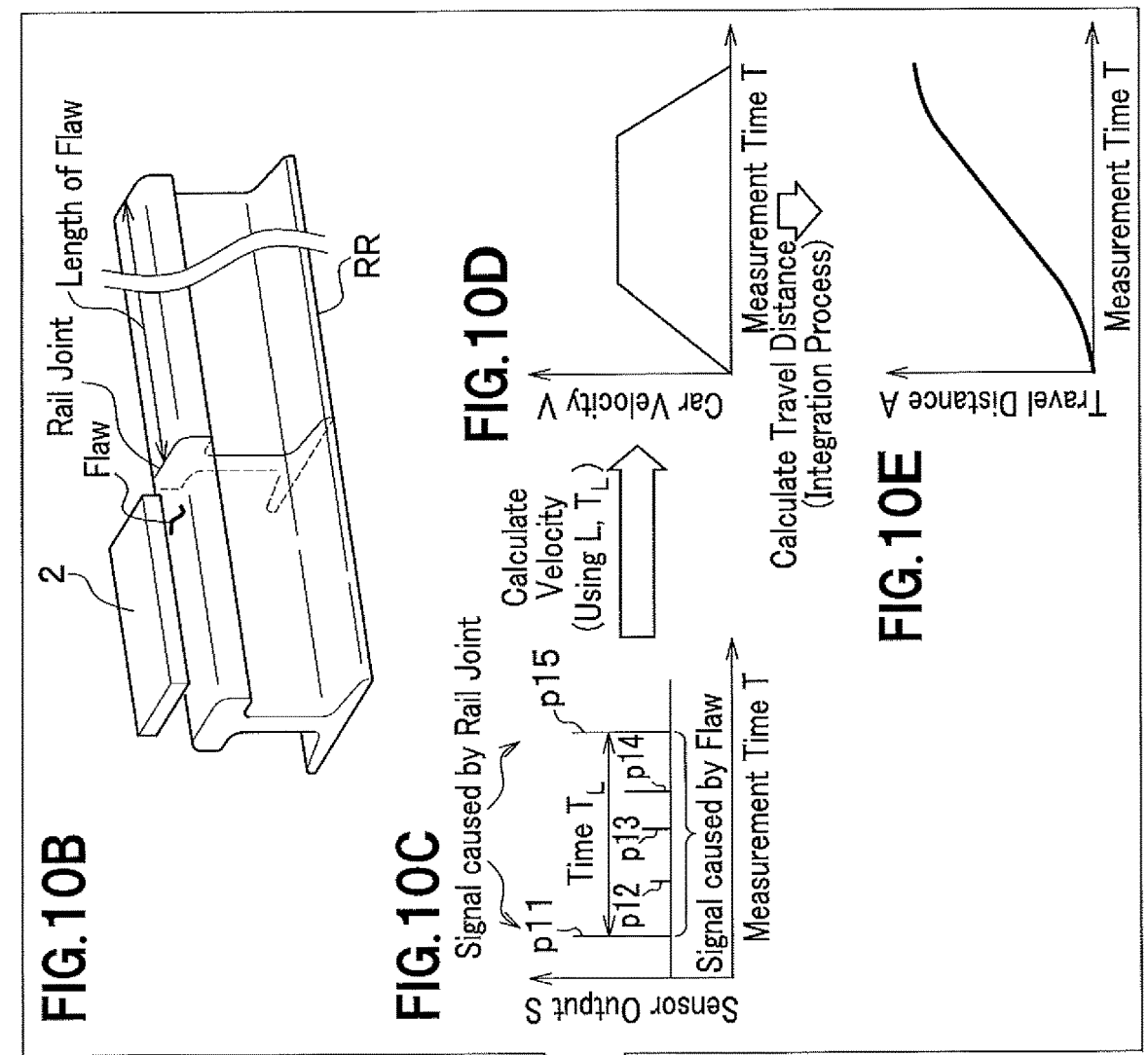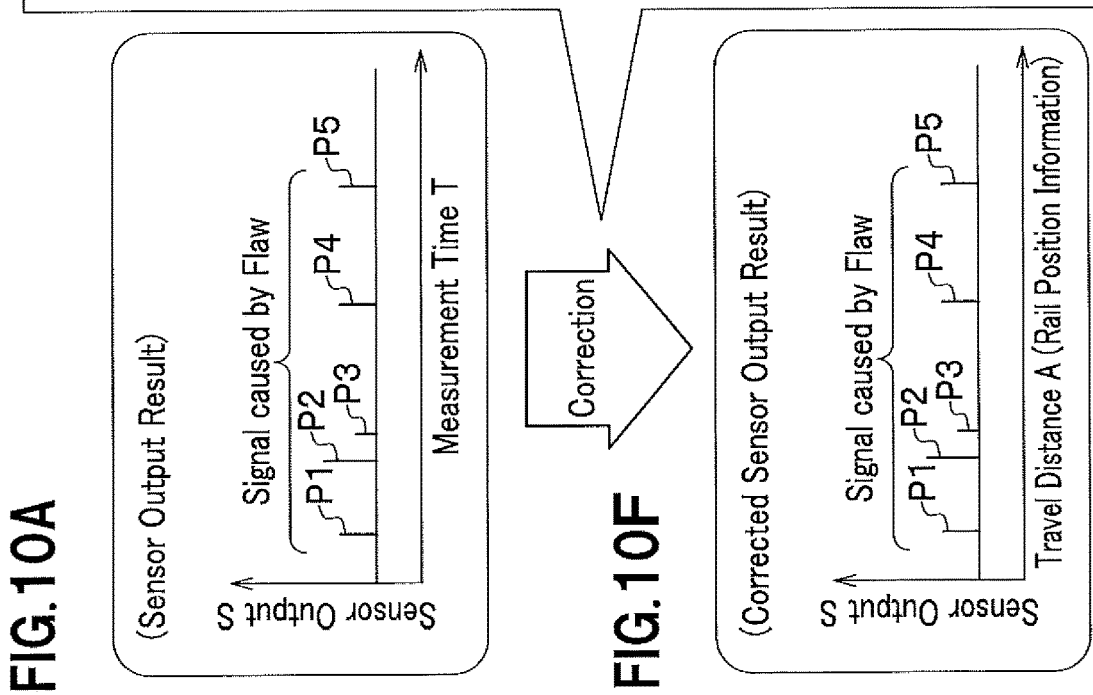

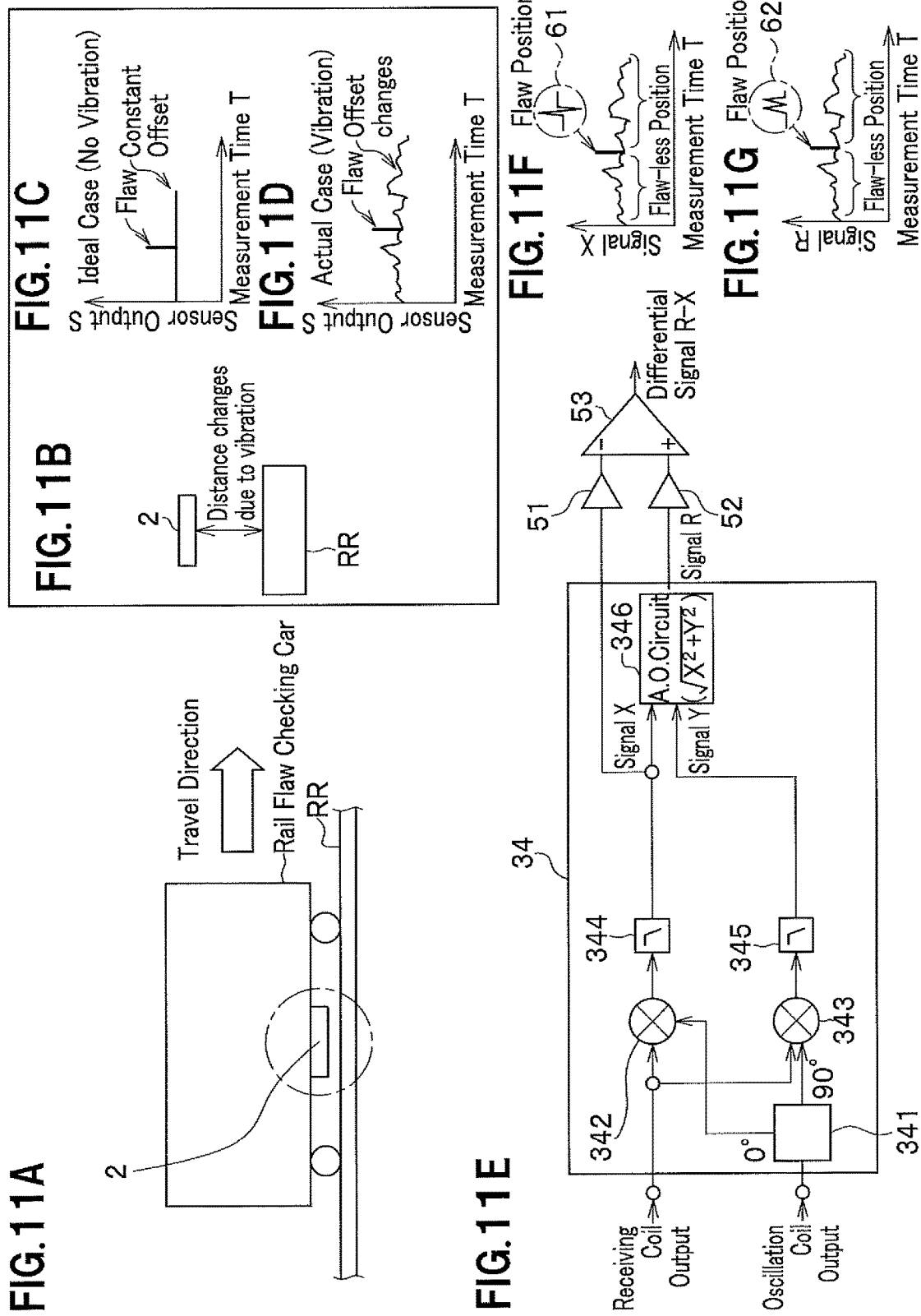

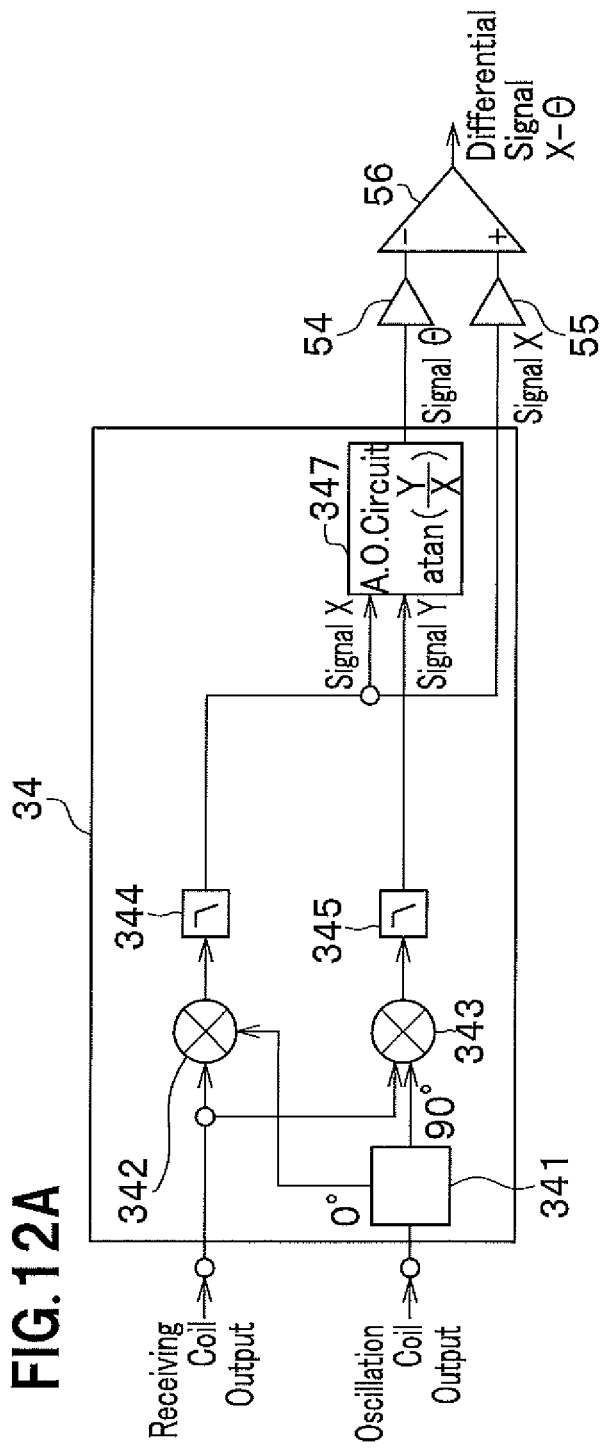

RAIL CHECK DEVICE AND RAIL CHECK SYSTEM

TECHNICAL FIELD OF THE INVENTION

The present invention relates to a technology with which a defect on a rail used for vehicles such as railway cars is checked.

DESCRIPTION OF THE RELATED ART

For instance, since a load of a railway car is applied to a rail (referred to as "railway rail" hereinafter) on which the railway car is running, it is necessary to check at regular intervals whether there is a defect (mechanical flaw) produced.

To carry out such a checking operation, there is a flaw checking method in which an ultrasonic probe is used. However there are various problems with this flaw checking method. First of all, measurements are being carried out while water is sprayed on the railway rail, the flaw checking cannot be performed for a long time due to a limitation of a water tank volume. Secondly, since the ultrasonic probe is in the vicinity of (or almost in contact with) the railway rail while the flaw checking is under way, there is a limit to the checking speed (maximum speed is approximately 40 km/h) even when a rail flaw checking car is used. Thirdly this flaw checking method is suited for detection of an inner flaw but not for a surface flaw.

There is a modified flaw checking method disclosed in the Patent document 1. According to this modified flaw checking method, while an alternating current magnetic field generated from an excited coil is being applied to a railway rail to generate an eddy current, a flaw of the railway rail is detected based on an amplitude change of a varying induced voltage that is induced by the eddy current and detected through a couple of detection coils disposed on both sides of the magnetically exciting coil the railway rail.

PRIOR ART DOCUMENTS

Patent Document

Patent Document 1: JP2014-102197A

SUMMARY OF THE INVENTION

Objective of the Invention to be Achieved

However, there is a following problem with the method disclosed in Patent Document When a railway rail is checked with a rail flaw checking car according to this method, a distance between each detection coil and a railway rail changes due to (vertical) vibration of the rail flaw checking car. There is a noise on the varying induced voltage, which is as big as in the order of a square of the change amount of the distance. As a result, it is hardly possible to perform the checking with a high SN ratio (Signal-Noise ratio).

The objective of the present invention is to enable checking on the defect of the railway rail at a higher SN ratio.

Means to Achieve the Objective

In order to achieve the objective, the present invention provides a rail check device to generate check data with respect to defects of a rail for vehicles. This rail check device has a feature of comprising a first oscillation coil and a second oscillation coil, which are disposed on a face opposite the rail that is a checked object and generate magnetic fields whose directions are opposite to each other and a receiving coil which is disposed between or in the vicinity of the first oscillation coil and the second oscillation coil and configured to output a magnetic field waveform as check data based on the magnetic fields received from the first oscillation coil and the second oscillation coil. Other features are explained below.

Effect of the Invention

The present invention enables checking a rail for vehicles with a high S/N ratio.

BRIEF DESCRIPTION OF THE DRAWINGS

FIG. 1 is a figure to illustrate a principle based on which check data for a defect on a checked object is generated using a couple of oscillation coils and a receiving coil.

FIG. 8 shows an example of a configuration of the detection device. FIG. 8A is a perspective view of the detection device while

FIG. 9 shows an example of a configuration of the detection device. FIG. 9A is a perspective view of the detection device while

FIGS. 10A to 10F illustrate how to determine a position of a flaw of the rail in the rail longitudinal direction relative to a position of a rail joint.

FIGS. 11A to 11G illustrate a first method to prevent accuracy with which a flaw is detected from lowering due to (vertical) vibration when a rail flaw checking car is running.

FIGS. 12A to 12C illustrate a second method to prevent accuracy with which a flaw is detected from lowering due to (vertical) vibration when a rail flaw checking car is running.

DETAILED DESCRIPTION OF THE INVENTION

Figure 2A:
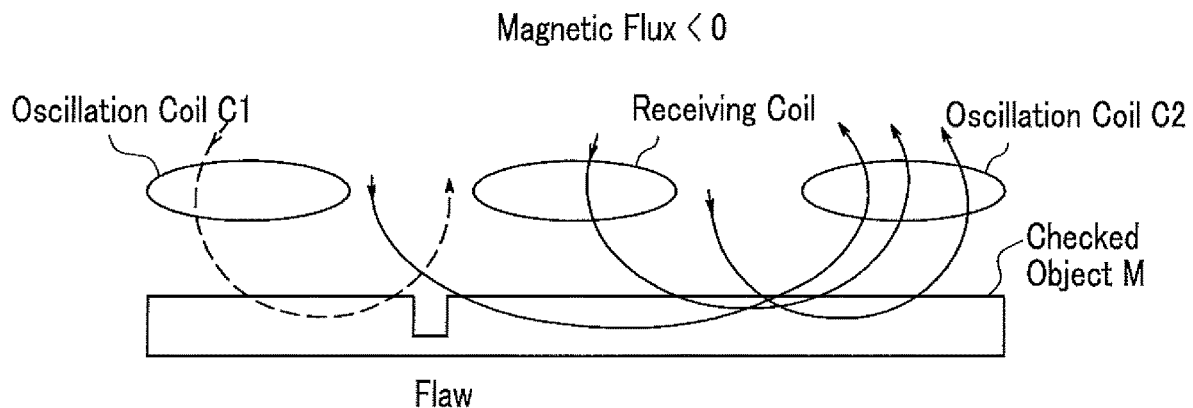
FIG. 2A, FIG. 2B and FIG. 2C are figures to illustrate directions of interlinkage flux through the receiving coil when there is a flaw on a checked object.

Hereinafter, embodiments to practice the present invention (referred to as "embodiments" hereinafter) are explained in detail, referring to attached figures.

Firstly, referring to FIG. 1, a principle of how check data on a defect on a checked object M (for example, railway rail) is obtained with a couple of oscillation coils and one receiving coil (referred to as "three coils" hereinafter).

As shown in FIG. 1, this embodiment has an oscillation coil C1 (First oscillation coil), a receiving coil and an oscillation coil C2 (Second oscillation coil), all of which are disposed opposite a checked object M and, for example, aligned in a longitudinal direction of the checked object M (lateral direction of FIG. 1).

The oscillation coil C1 and the oscillation coil C2 are configured to generate alternating current magnetic fields whose directions are opposite to each other.

The receiving coil is disposed between the oscillation coil C1 and the oscillation coil C2 and outputs a magnetic field waveform according to magnetic fields received from the oscillation coil C1 and the oscillation coil C2.

Magnetic field lines B1, B2, B3 generated from the oscillation coil C1 run through the checked object M, leak out of the object M and come back through the oscillation coil C1. Sizes of the magnetic field lines coming back through the oscillation coil C1 are dependent on the cross section and the height h (distance from the checked object M to the oscillation coil C1) of the checked object M. In addition, the closer a point is to the oscillation coil C1, the stronger the magnetic field at the point. Therefore, the magnetic field lines have a magnitude relation of their magnetic fields of B3<B2<B1.

Similarly, magnetic field lines B11, B12, B13 generated from the oscillation coil C2 run through the checked object M, leak out of the checked object M and come back through the oscillation coil C2. In addition, the magnetic field lines B11, B12, B13 have a magnitude relation of their magnetic fields of B13<B12<B11.

In FIG. 1, an upper direction is assumed to be a positive direction of the magnetic field, and the oscillation coil C1 and the oscillation coil C2 are assumed to generate the alternating current magnetic fields that are equal to each other. Hereinafter, the following case is considered. That is, at a certain moment a magnetic field that comes into the oscillation coil C1 from an upper side thereof and runs through the oscillation coil C1 is generated from the oscillation coil C1 and simultaneously the other magnetic field that comes into the oscillation coil C2 from a lower side thereof and runs through the oscillation coil C2 is generated from the oscillation coil C2.

In this case, looking to positions between the oscillation coil C1 and the receiving coil, the magnetic field line B1 and the magnetic field line B13 offset each other and the magnetic field line B1 is stronger at the positions. Accordingly there remains a magnetic field line directed upward (B1+B13>0).

Then looking to positions between the oscillation coil C2 and the receiving coil, the magnetic field line B3 and the magnetic field line B11 offset each other and the magnetic field line B11 is stronger at the positions. Accordingly there remains a magnetic field line directed downward (B3+B11<0).

In addition, looking to the receiving coil, the magnetic field line B2 and the magnetic field line B12, which are as strong as each other, offset each other. Accordingly, there remains no magnetic field line (B2+B12=0) in the receiving coil, which indicates that if the checked object M has no defect there is no electrical current flowing through the receiving coil.

Figure 2B:
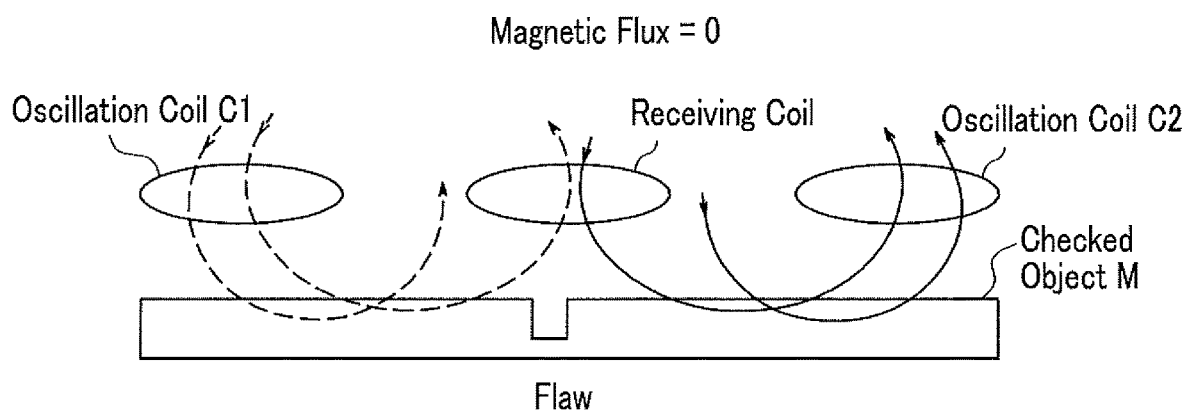
Figure 2C:
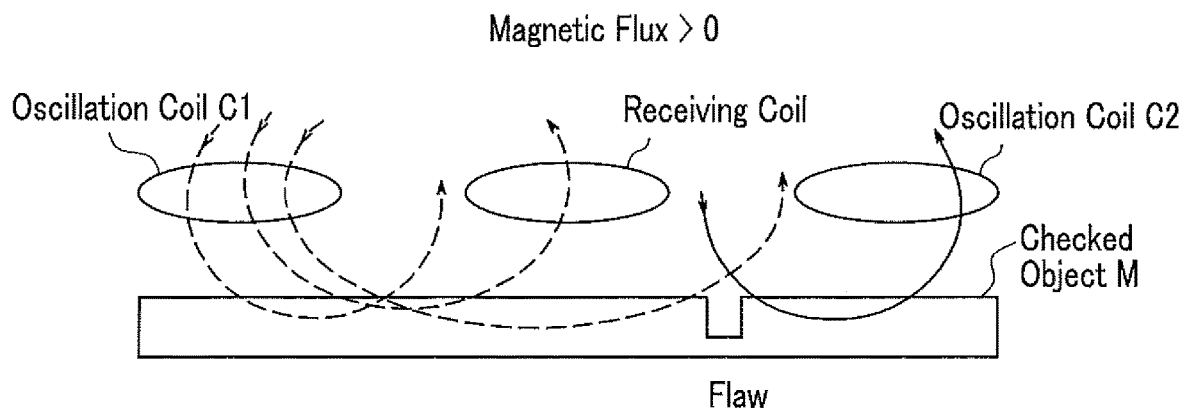

Next, referring to FIG. 2A to FIG. 2C, an explanation is given on a case where there is a flaw on the checked object M. Hereinafter interlinkage flux that interlinks with the receiving coil is represented by $\Phi$.

As shown in FIG. 2A, when there is a flaw on the checked object M between the oscillation coil C1 and the receiving coil, part of the magnetic field lines generated from the oscillation coil C1 and running through the checked object M come upward out of the flaw, which results in the magnetic flux $\Phi<0$.

Next as shown in FIG. 2B, when there is a flaw on the checked object M just under the receiving coil, the magnetic flux $\Phi=0$.

Then, as shown in FIG. 2C, when there is a flaw on the checked object M between the oscillation coil C2 and the receiving coil, the magnetic flux $\Phi>0$.

Figure 3:
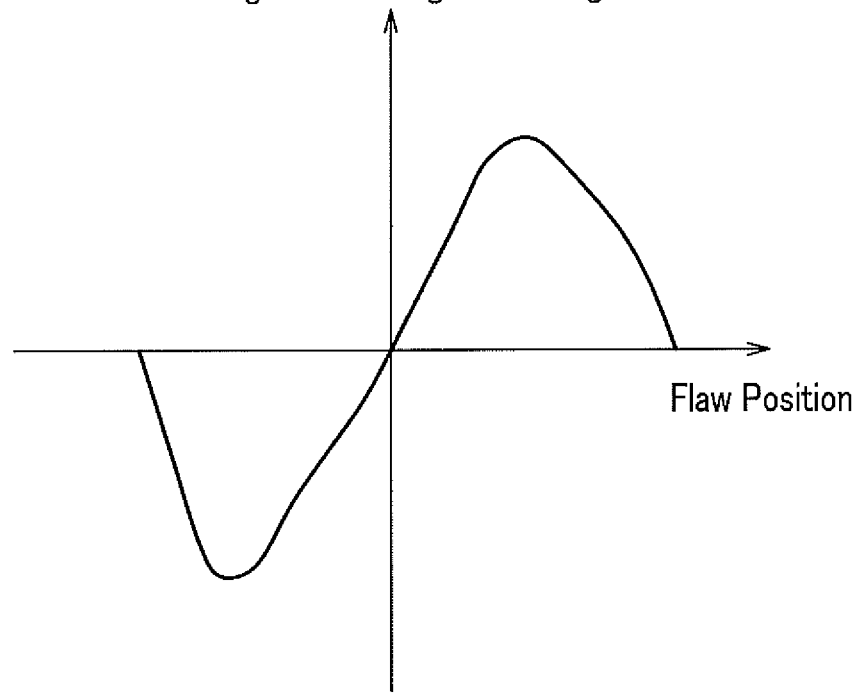
FIG. 3 is a graph indicating a relation between interlinkage flux interacting with the receiving coil and a position of a flaw in the case of FIGS. 2A, 2B, 2C.

In these cases, the relation between the interlinkage flux through the receiving coil and the position at which the flaw exists (reference point is set to the center of the receiving coil) is approximately shown in FIG. 3.

Therefore it is possible to identify the position of the defect on the checked object M based on how the current outputted from the receiving coil (magnetic field waveform) changes over time. That is, if the checked object M has a defect, the magnetic field waveform outputted from the receiving coil changes greatly (for example, see FIG. 10A). As has been explained, based on the configuration in which the alternating current magnetic fields generated from the oscillation coil C1 and the oscillation coil C2, whose directions are opposite to each other, offset each other at a position of the receiving coil, it is possible to obtain check data for locating a defect on or in the checked object M with a higher SN ratio.

If the magnitudes of the magnetic fields generated from the oscillation coil C1 and the oscillation coil C2 are equal to each other, the interlinkage flux $\Phi$ through the receiving coil is not 0 even for the checked object M without a defect (no flaw is included) when the receiving coil is offset in the direction of either of the oscillation coil C1 and the oscillation coil C2 from the center between the oscillation coil C1 and the oscillation coil C2. However, even when the receiving coil is offset toward either of the oscillation coil C1 and the oscillation coil C2 from the center between the oscillation coil C1 and the oscillation coil C2, it is possible to adjust the magnetic flux through the receiving coil to 0 ($\Phi=0$) by modifying the alternating current magnetic field generated by one of the oscillation coil C1 and the oscillation coil C2 to be stronger than the alternating current magnetic field generated by the other, as long as the offset magnetic flux is so small as to get the magnetic flux through the receiving coil adjusted to 0 by amplifying or processing of the oscillation coils. Accordingly, the receiving coil does not necessarily have to be disposed at the exact center between the oscillation coil C1 and the oscillation coil (C2 and may be disposed in the vicinity of the center between the oscillation coil C1 and the oscillation coil C2. When the offset of the receiving coil from the center between the oscillation coil C1 and the oscillation coil C2 is sufficiently small, it is possible to obtain usable check data with the magnitudes of the alternating current magnetic fields generated from the oscillation coil C1 and the oscillation current C2 being kept equal to each other (magnetic flux $\Phi \neq 0$).

In FIG. 1 and FIG. 2B, the magnetic flux is assumed to be 0 in the receiving coil (B2+B12=0, magnetic flux Φ=0). However there can be a case where the magnetic flux is not exactly 0 and current flows through the receiving coil because of the influence of the peripheral environment. That is, as shown in FIG. 10A, there is always an offset current flowing through the receiving coil in this case. FIG. 10A schematically shows sensor outputs S which correspond to squared actual output values. However, even when there is always an offset included in the sensor output from the receiving coil, it is still the case that the magnetic fluxes from the oscillation coil C1 and the oscillation coil C2 offset each other in the receiving coil and the total magnetic flux through the receiving coil is closer to 0 than when there is only one oscillation coil. Furthermore, there is no difference in how the magnetic flux through the receiving coil changes, whether there is a flaw of the checked object M. Accordingly a flaw of the checked object M is identified with a high SN ratio.

Figure 4:
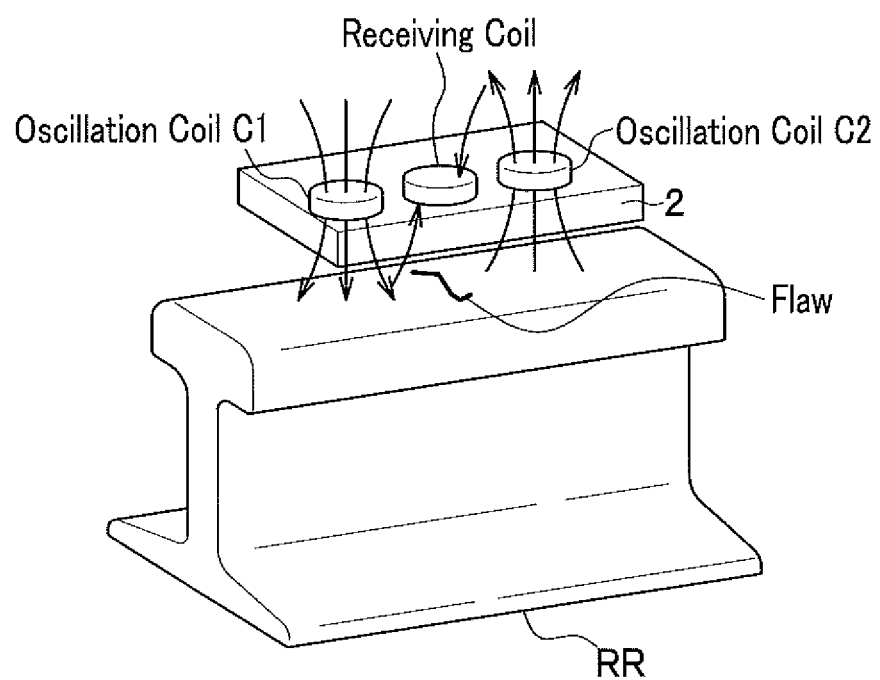
FIG. 4 is a figure indicating a configuration where a detection device is disposed opposite an upper face of the railway rail.

Next is explained how a detection device inclusive of the three coils is disposed at a position opposite the upper face of the railway rail. For example, a detection device 2 (rail check device) inclusive of the three coils is disposed opposite the upper face of the railway rail RR as shown in FIG. 4. This detection device 2 is, for example, secured onto the bottom of and outside the rail flaw checking car.

When the rail flaw checking car is running along the railway rail RR, check data for the defect is obtained according to the change in the magnetic waveform outputted from the receiving coil at a position where there is a flaw.

Figure 5:
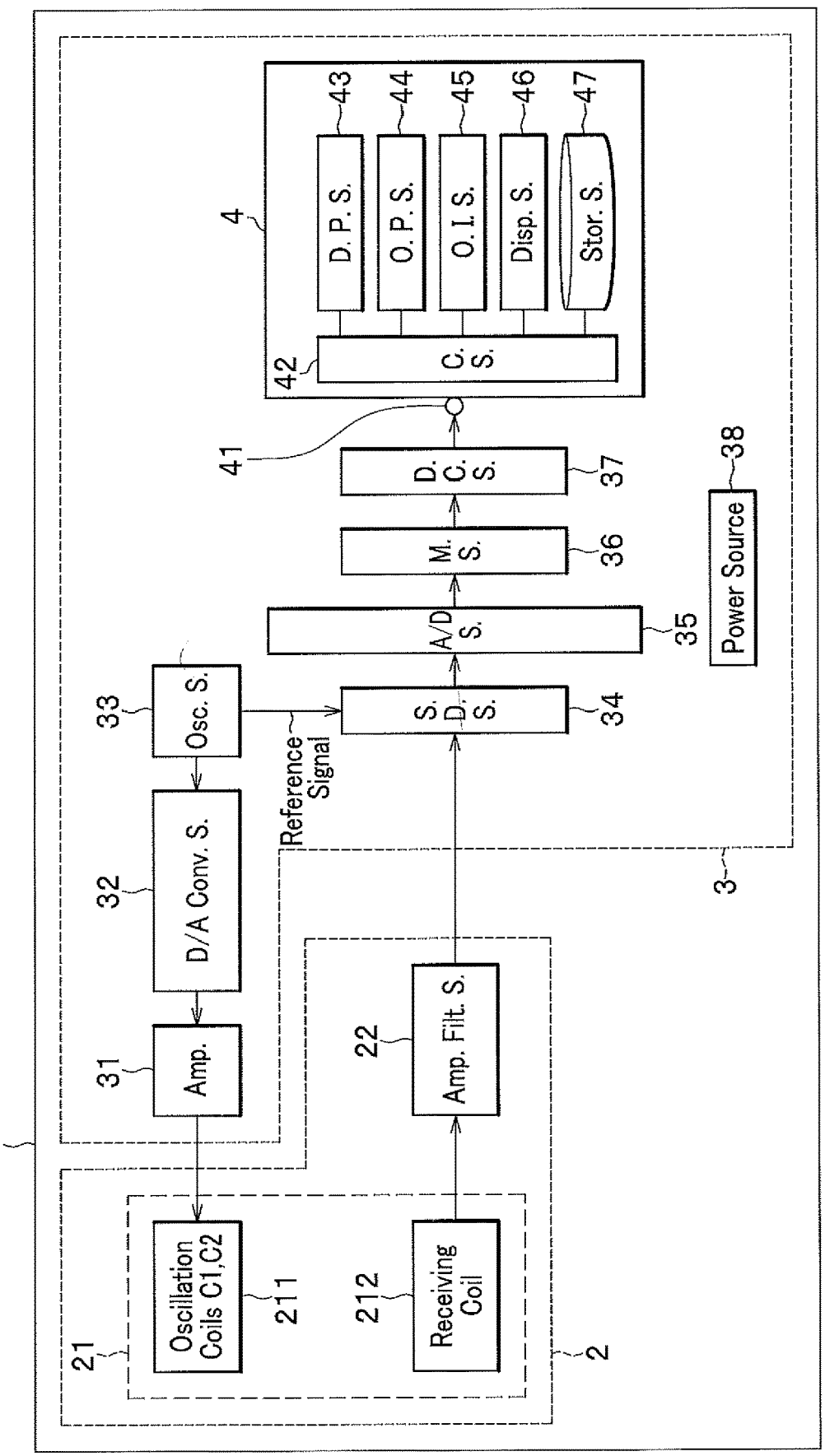
FIG. 5 is a block diagram showing a whole configuration of a rail check system with one sensor section (one channel).
Figure 7:
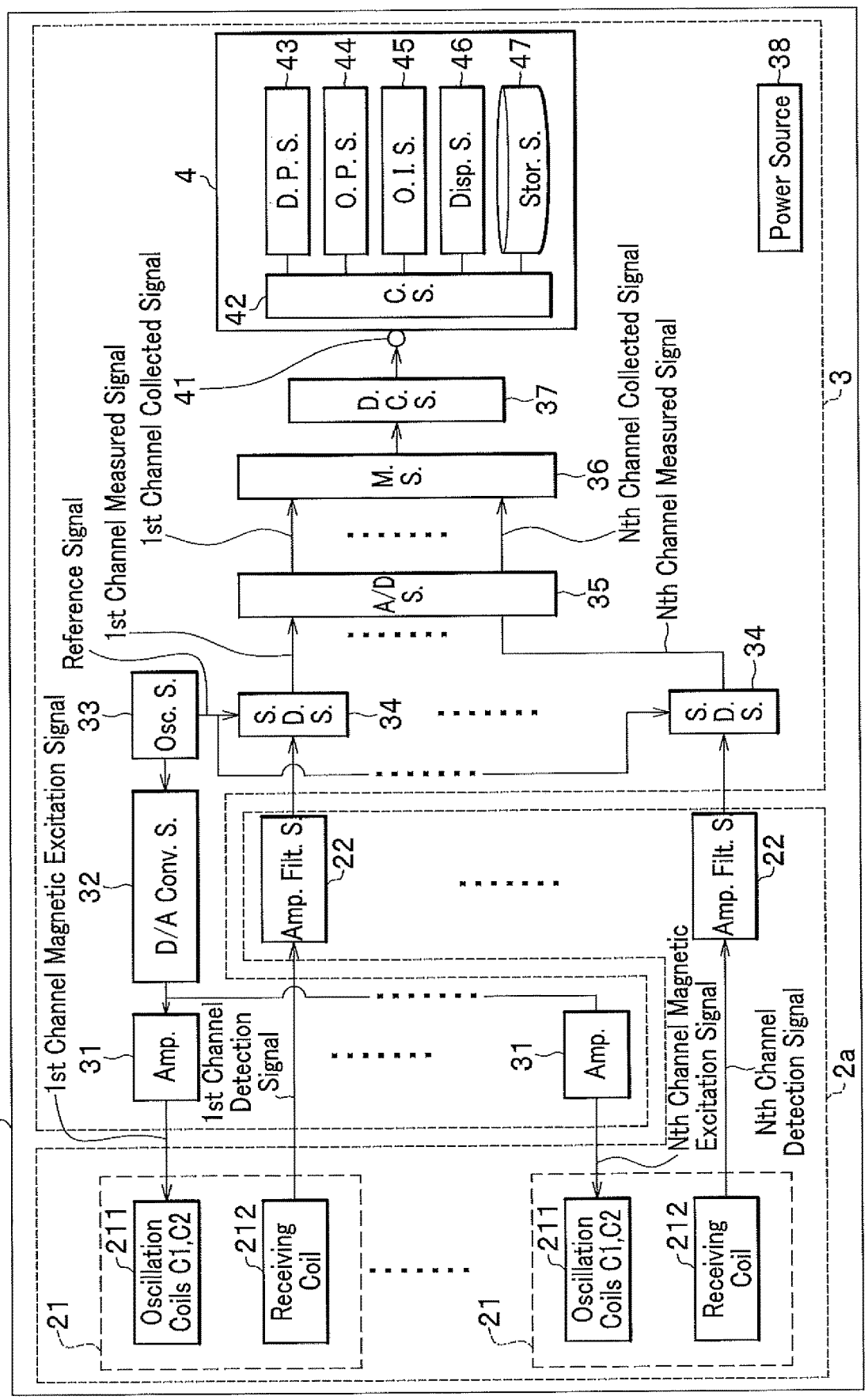
FIG. 7 is a block diagram showing a whole configuration of a rail check system with plural sensor sections (multi-channel).

Next is explained a whole configuration of the rail check system of the present embodiment. As shown in FIG. 5, a rail check system 1 for checking on the defect of the railway rail comprises the detection device 2 and a signal processing device 3. The rail check system 1 as indicated in FIG. 5 is different from a rail check system 1a having plural sensor sections 21 (multi-channel) as indicated in FIG. 7, since the rail check system 1 has only one sensor section 21 (one channel).

The detection device 2 is a device for obtaining check data for a defect of the railway rail RR, comprises a sensor section 21 and an amplification and filtering section (Amp. Filt. S.) 22 and is, for example, secured on the bottom of the rail flaw checking car and on the outer side of the rail flaw checking car.

The sensor section 21 comprises a oscillation coil C1 211 and an oscillation coil C2 211 which are disposed on a plane opposite the railway rail RR, aligned along the direction in which the railway rail extends and generate alternating current magnetic fields whose directions are opposite to each other, and a receiving coil which is disposed between or in the vicinity of the oscillation coil C1 211 and the oscillation coil C2 211 and outputs a magnetic waveform as the check data based on the magnetic fields from the oscillation coil C1 211 and the oscillation coil C2 211 (See FIG. 4).

The oscillation coils C1 211, C2 211 correspond respectively to the oscillation coil C1 and the oscillation coil C2 which are shown in FIG. 4. There might be a case where the sign of "211" is skipped below. The receiving coil 212 corresponds to the receiving coil as shown in FIG. 4. There might be a case where the sign of "212" is skipped in the explanation below.

The amplification and filtering section 22 is configured to amplify and filter a signal received from the receiving coil and transmit the amplified and filtered signal to a signal detection section (S.D.S) 34.

The signal processing device 3 comprises an amplification section (Amp. S.) 31, a digital/analogue conversion section (D/A Cony. S.) 32, an oscillation section (Osc. S.) 33, a signal detection section 34, an analogue/digital conversion section (A/D Cony. S.) 35, a memory section (M. S.) 36, a data communication section (D. C. S.) 37, a power source section 38 and an evaluation device 4 and installed, for example, in the rail flaw checking car.

The oscillation section 33 is configured to transmit digital oscillation signals at a predetermined frequency (for example, 20 kHz).

The digital/analogue conversion section 32 is configured to convert the digital oscillation signal received from the oscillation section 33 to an analogue alternating current.

The amplification section 31 is configured to amplify the alternating current received from the digital/analogue conversion section 32 and have the amplified alternating current flow through the oscillation coils C1, C2.

The oscillation coils C1, C2, through both of which the alternating currents flow, generate magnetic fields whose directions are opposite to each other. One way to have the oscillation coils C1, C2 generate the magnetic fields whose directions are opposite to each other is to have the oscillation coils C1, C2 wound in opposite directions to each other.

Output signals (magnetic field waveform) outputted from the receiving coil in accordance with the magnetic fields generated by the oscillation coils C1, C2 and coming into the receiving coil are amplified and filtered through the amplification and filtering section 22 and inputted to the signal detection section 34.

The signal detection section 34 is configured to perform a full-wave rectification process and a filtering process (mainly low-pass filter process) using a reference signal received from the oscillation section 33.

The analogue/digital conversion section 35 converts the analogue signal received from the signal detection section 34 to a digital signal.

Data (digital signal) after the conversion by the analogue/digital conversion section 35 is stored on the memory section 36 and outputted from the data communication section 37 to the evaluation device 4.

The power source 38 supplies power to each section in the rail check system 1.

Next is explained the evaluation device 4. The evaluation device 4 is a computer device to perform a checking process to locate a defect on the railway rail based on the check data received from the detection device 2. The evaluation device 4 comprises a data input section 41, a control section (C. S.) 42, a data processing section (D. P. S.) 43, an output process section (O. P. S.) 44, an input operation section 45, a display section (Disp. S.) 46 and a storage section (Stor. S.) 47. In this embodiment, check data indicate data dealt with at any stage between the receiving coil of the detection device 2 and the data input section 41 of the evaluation device 4.

The output signal (check data) from the data communication section 37 is inputted at the data input section 41.

The control section 42 comprises CPU (Central Processing Unit), RAM (Random Access Memory) and ROM (Read Only Memory) and is configured to control such operations as data transfer and arithmetic operation.

The data processing section 43 is configured to perform the check operation (to be explained below) based on the output signal (check data). Information such as check results is stored in the storage section 47 when needed.

The output process section 44 is configured to perform operation to display on the display section 46 such data as check results in a display form with which it is easy to visually understand the displayed data, using graphs and tables appropriately.

The input operation section 45 is such information input means as a keyboard or mouse.

The display section 46 is such a display to display check results or the like as LCD (Liquid Crystal Display) and CRT (Cathode Ray Tube).

The storage section 47 is a section on which data after processed by the data processing section 43 and the like is stored.

Both the data processing section 43 and the output process section 44 are configured to perform their functions by loading a program and data to the control section 42 and have the control section 42 perform an arithmetic operation.

Figure 6:
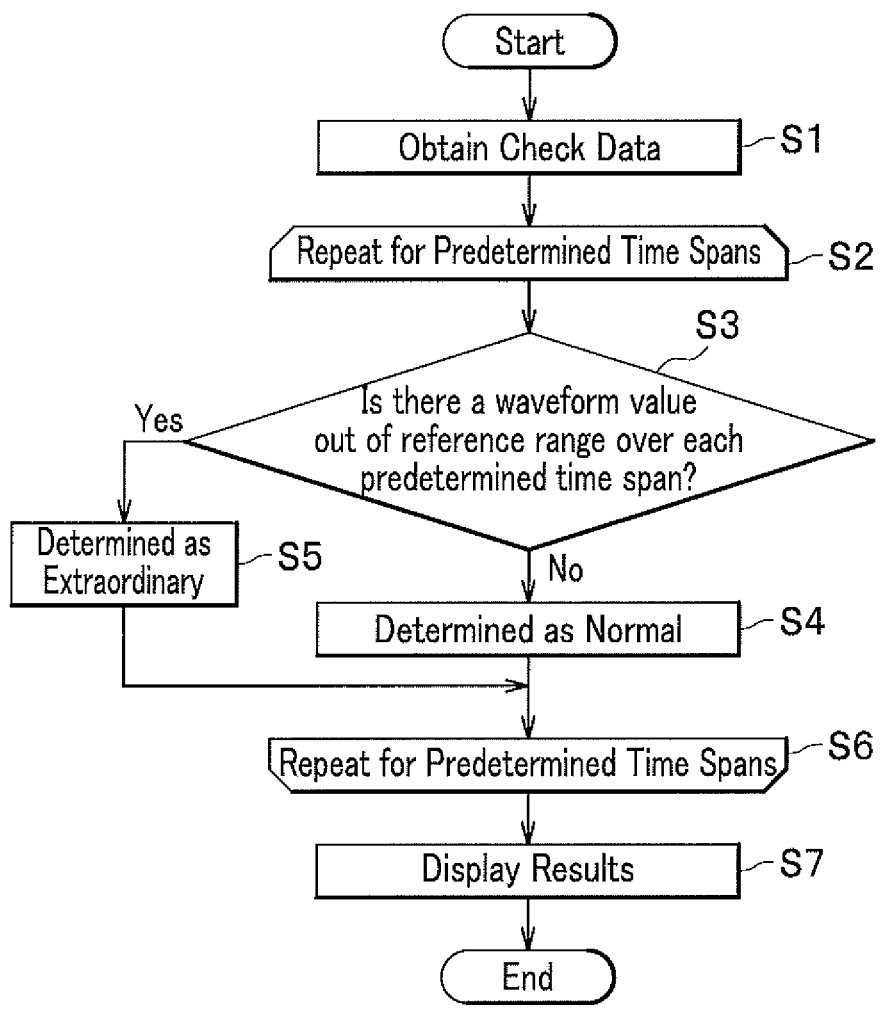
FIG. 6 is a flowchart describing a check process for locating a defect of the railway rail with an evaluation device.

Next is explained the check operation by the data processing section 43 of the evaluation device 4, referring to FIG. 6 (additionally See FIG. 5 when needed).

To begin with, the data processing section 43 obtains check data from the storage section 47 (Step S1). In this step may be performed an offset control process, in which a signal of the offset explained above and included in the check data is lowered.

Next, the data processing section 43 performs the following steps S3 to S5 over each of the predetermined time spans such as 0.5 ms-100 ms (Step S2-Step S6).

The data processing section 43 is configured to determine whether there is a waveform value out of the reference range in the check data over each of the predetermined time spans (Step S3). As a result of this determination, if there is no waveform value out of the reference range (No), the data processing section 43 determines that no defect exists (Step S4). On the other hand, if there is a waveform value out of the reference range, the data processing section 43 determines that there exists a defect (Step S5).

When the processes of Steps S3 to S6 are finished for all the check data, the data processing section 43 displays the result of the check data on the display section 46.

Next, referring to FIG. 7, a configuration of a rail check system 1a with plural sensor sections 21 (Multi-channel) is explained. Features of this system that are different from those of the rail check system in FIG. 1 is mainly explained and explanation of other features is skipped if not needed.

The rail check system 1a comprises a sensing device 2a that is attached on the bottom of and outside the flaw checking car. The sensing device 2a includes as many as N sensor sections 21 (1~N channel). As a result, the sensing device 2a further includes as many amplification and filtering sections 22 as N and the processing device 3 includes N amplification sections 31 and N signal detection sections 34.

The digital/analogue conversion section 32 is configured to convert the digital oscillation signal received from the oscillation section 33 to an analogue alternating current and transmit the alternating current to each of the N amplification sections 31.

Each of the N amplification sections 31 transmits a magnetic excitation signal (alternating current) for each channel to its corresponding oscillation coils (1), (2) 211.

Each receiving coil 212 transmits a detection signal for each channel (output signal (magnetic field waveform)) to its corresponding signal detection section 34 through the amplification and filtering section 22.

The analogue/digital conversion section 35 receives from each signal detection section 34 a measured signal (analogue signal) for the corresponding channel, converts the measured signal to collected data (digital signal) for the corresponding channel and transmits the collected signal to the storage section 36 where the collected data is stored.

The evaluation device 4 performs the check process to locate a defect of the railway rail (as described in FIG. 6) on the collected data (check data) from each channel.

Since the rail check system 1a has plural sensor sections 21 (multi cannels), it can detect a defect of the railway rail with higher accuracy. Hereinafter a specific configuration is explained in detail.

Figure 8A:
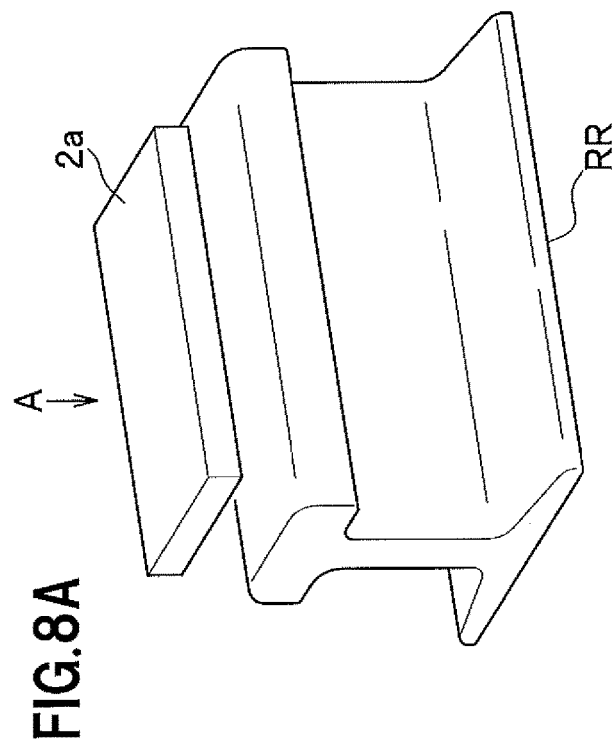
Figure 8B:
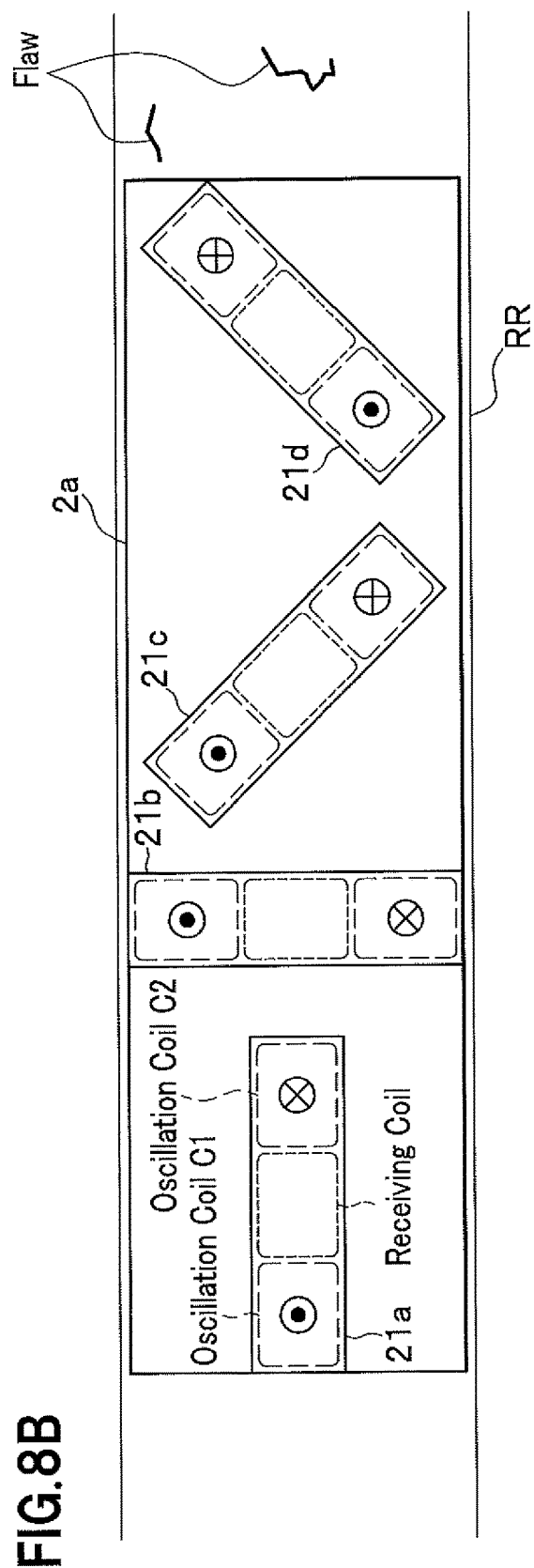
FIG. 8B is a plan view of the detection device when it is viewed from the A direction indicated in FIG. 8A.

As shown in FIGS. 8A, 8B, a detection device 2a comprises 4 sensor sections 21a to 21d and disposed at a position over and opposite the upper face of the railway rail RR. This detection device 2a is mounted on the bottom of and outside the rail flaw checking car.

The sensor section 21a is disposed in parallel with the longitudinal direction of the railway rail RR.

The sensor section 21b is disposed in a direction that is orthogonal to the longitudinal direction of the railway rail RR.

The sensor section 21c is disposed in a diagonal direction that makes an angle of 45 degrees to the longitudinal direction of the railway rail RR.

The sensor section 21d is disposed in a diagonal direction that is orthogonal to the sensor section 21c.

As explained above, though the detection device 2a makes use of the sensor sections 21a to 21d whose width is smaller than the width of the railway rail RR, the detection device 2a is capable of detecting with high accuracy a defect of the railway rail that is located at any position in the width direction of the rail way rail RR or is in any shape since it has the plural sensor sections 21a to 21d oriented in different directions that are different from one another as shown in FIG. 8B. It is noted that the number of the sensor sections and how these sensors are arranged are not limited to the sensor sections 21a to 21d as shown in FIG. 8B.

Figure 9A:
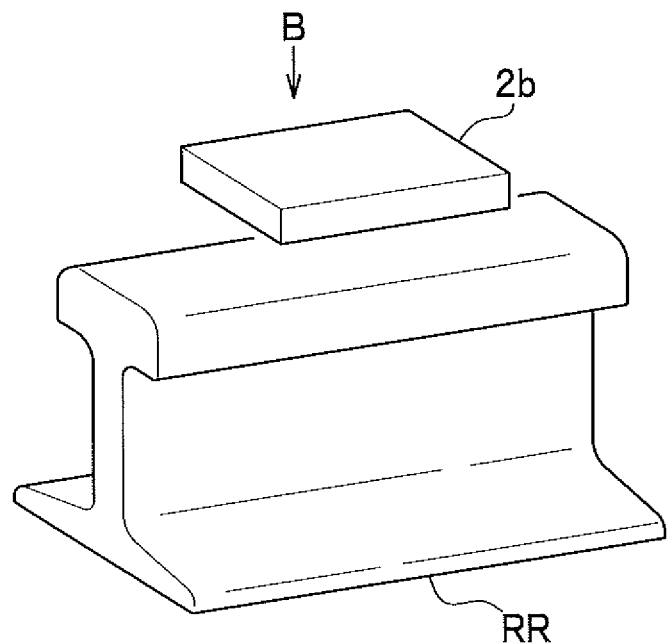
Figure 9B:
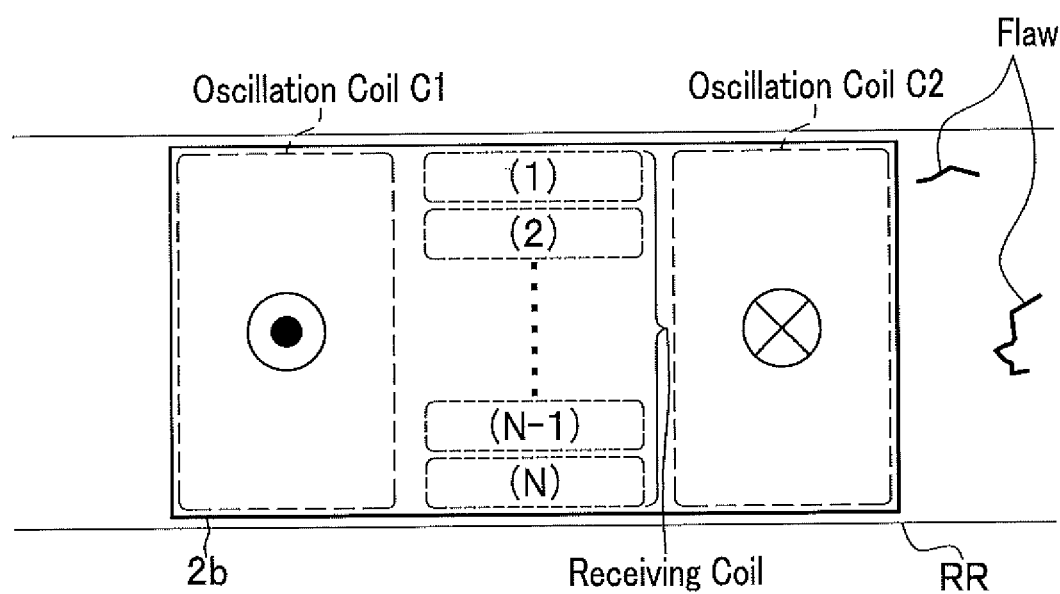
FIG. 9B is a plan view of the detection device when it is viewed from the B direction in FIG. 9A.

Next is explained another example of a specific configuration of the detection device. As shown in FIGS. 9A, 9B, a detection device 2b comprises an oscillation coil C1 and an oscillation coil C2, whose longitudinal length is so large as to cover the width of the railway rail RR, and N independent receiving coils arranged in parallel with one another and in the width direction of the railway rail RR. This detection device 2b is mounted, for example, on the bottom of and outside the rail flaw checking car. The rail check system with this detection device 2b is different from the rail check system 1a shown in FIG. 7, since it has only one set of the oscillation coils C1, C2 and only one amplification section 31 for them. Except for the numbers of the amplification sections 31 and the sets of the oscillation coils C1, C2, the rail check system with this detection device 2b is the same as the rail check system 1a and is not indicated with a figure.

According to the detection device 2b indicated in FIGS. 9A and 9B, when there is a flaw on the railway rail RR, a signal that is influenced by the flaw is outputted by one of the receiving coils that is disposed over a position in the width direction on the railway rail RR where the flaw exists. Accordingly, wherever a flaw exists in the width direction on the railway rail, it is possible to detect the flaw with high accuracy and determine the position in the width direction where the flaw exists. Furthermore, since the detection device 2b needs only one set of the oscillation coils C1, C2 and only one amplification section 31, the whole circuit is made smaller, which contributes to low power consumption, low cost and a compact system.

Technical contents explained below referring to FIG. 10A to FIG. 14 are common to any of the rail check system 1 as shown in FIG. 5, the rail check system 1a as shown in FIG.

7 and the rail check system with any of the detection device 2*a* in FIGS. 8A, 8B and the detection device 2*b* in FIGS. 9A, 9B.

Referring to FIGS. 10A to 10F, a flaw location method is explained. The flaw location method is intended to determine a position in the rail longitudinal direction (hereinafter may be referred to as "longitudinal direction position") where a flaw is when the flaw is detected on or in the railway rail RR.

For example, as shown in FIG. 10A, the output signal from the receiving coil is indicated in a graph having the sensor output on a vertical axis and a measurement time (time of measurement) T on a horizontal axis. In FIG. 10A, sensor outputs P1 to P5 indicate signals caused by flaws. However, flaws cannot be located in the rail longitudinal direction with this graph.

For the purpose of locating the flaws, signals resulting from rail joints of the railway rail are utilized. As indicated in FIG. 10B, there usually exist rail joints between railway rails RR at constant intervals (L) due to such a reason as for rail production. Positions of the rail joints in the rail longitudinal direction are known. It is found that P11, P15 that are sensor outputs S influenced by the rail joints are significantly larger than P12 to P14 that are sensor outputs S influenced by flaws as indicated in FIG. 10C. In this measurement, a time between P11 and P15 is assumed to be $T_L$.

As shown in FIG. 10D, a relation between a speed (V) of a train (rail flaw checking car) and a measurement time T is obtained using L and $T_L$. Integrating the speed (V), a relation between a travel distance (A) and the measurement time (T) is obtained, as shown in FIG. 10E.

Combining the relation between the sensor output S and the measurement time T indicated in FIG. 10A with the relation between the travel distance A and the measurement time T as indicated in FIG. 10E, a relation between the sensor output S and the travel distance A (rail longitudinal direction position) is obtained as shown in FIG. 10F.

As explained, making use of information on the position in the rail longitudinal direction at which the rail joint is, it is possible to locate a flaw of the railway rail RR in the rail longitudinal direction.

Next is explained a first method to prevent accuracy with which the flaw is detected from lowering due to vibration of the rail flaw checking car that is running, referring to FIGS. 11A to 11G. Since the magnetic fields from the oscillation coils C1, C2, whose directions are opposite to each other, offset each other in the receiving coil according to the flaw detection principle of the present embodiment as explained in FIG. 1 to FIG. 3, the output signal is inherently unlikely to be influenced by a noise caused by the (vertical) vibration of the rail flaw checking car, even when the rail flaw check is performed by the rail flaw checking car. A further improvement for the flaw checking is explained hereinafter.

As is shown in FIG. 11A and FIG. 11B, when the rail flaw checking car is running, a distance between the detection device 2 (sensor section 21) mounted on the bottom of and outside the rail flaw checking car and the upper face of the rail is changing due to the (vertical) vibration.

As shown in FIG. 11C, it is ideal to keep the offset of the sensor output S constant when there is no (vertical) vibration. When the offset is constant, it is easy to distinguish the output signal caused by the flaw.

However, since there is the (vertical) vibration, the offset included in the sensor output S changes as indicated in FIG. 11D and it is not easy to distinguish the output signal caused by the flaw.

If a comparison is made between the signal X and the signal R (equal to a square root of $(X^2+Y^2)$), there is a difference in the waveform shape for a flaw between these signals while there is no difference in the waveform shape for the other portions than the flaw between these signals. Making use of this property, it is possible to identify a signal for a flaw in the sensor output S, which is explained in detail below.

As is indicated in FIG. 11E, the signal X corresponds to a cosine component of the input signal, that is, the output of the receiving coil. This cosine component is synchronized with the magnetic field that is excited by the oscillation coils C1, C2 (phase difference equal to 0). Specifically, a phase comparison unit 342 receives the output of the receiving coil and 0 degree phase information from a component division unit 341 that receives the oscillation output and outputs the cosine component of the output of the receiving coil. The output of the phase comparison unit 342 passes through a low-pass filter circuit 344 and is inputted as the signal X to a gain adjustment circuit 51 and an arithmetic operation circuit 346.

A signal Y corresponds to a sin component of the input signal (output signal of the receiving coil), whose phase is shifted from the magnetic field by 90 degrees. Specifically, a phase comparison unit 343 receives the output of the receiving coil and 90 degrees phase information from the component division unit 341 that receives the oscillation output and outputs the sine component of the receiving coil. The output of the phase comparison unit 343 passes through the low-pass filter circuit 345 and is inputted as the signal Y to the arithmetic operation circuit 346.

The signal R (equal to a square root of $(X^2+Y^2)$) corresponds to an amplitude value of the output of the receiving coil and is generated by the arithmetic operation circuit 346 to which the signals X, Y are inputted. The signal R generated by the arithmetic operation circuit 346 is inputted to the gain adjustment unit 52.

As is understood by making a comparison between a graph of the signal X shown in FIG. 11F and a graph of the signal R shown in FIG. 11G, there is a difference only in the waveform shape for the flaw between these signals (See sign 61 and sign 62) and no difference in the waveform shape for the other portions than the flaw between these signals. It should be noted that there is a difference in the scale between the signal X and the signal R and that gains of these signals are appropriately adjusted by a gain adjustment sections 51, 52 so as to make these signals have the same scale. A differential signal generating unit 53 generates a differential signal (R−X) after the gain adjustments are performed on the signals R, X. Then a deviation of the differential signal (R−X) for the flaw from 0 is so much larger than that for the other points that the flaw can be identified.

Next is explained a second method to prevent accuracy with which the flaw is detected from lowering due to (vertical) vibration while the rail flaw checking car is running. FIGS. 12A to 12C are associated with FIGS. 11E to 11G. While the signal X and the signal R (=a square root of $(X^2+Y^2)$) are compared in the first method, a comparison is made between the signal X and a signal Θ (=a tan(Y/X)) in the second method. A duplicate explanation that has been made for FIGS. 11E to 11G is omitted below.

The signal Θ indicates a phase difference of the inputted signal from the reference signal (outputted from the oscillation section 33 in FIG. 5 and FIG. 7) and is generated by an arithmetic operation circuit 347 to which the signal X and the signal Y are inputted. The signal Θ generated by the arithmetic operation circuit 347 is inputted to a gain adjustment section 54, while the signal X is inputted to a gain adjustment section 55.

As is understood from a comparison between a graph of the signal X shown in FIG. 12B and a graph of the signal Θ shown in FIG. 12C, there is a difference only in the waveform shape for a flaw between these signals (See sign 63 and sign 64) and no difference for the other points than the flaw between these signals. It should be noted that there is a difference in the scale between the signal X and the signal Y and that gains of these signals are appropriately adjusted by a gain adjustment sections 54, 55 so as to make these signals have the same scale. A differential signal generating unit 56 generates a differential signal (X−Θ) after the gain adjustments are performed on the signals X, Θ. Then a deviation of the differential signal (X−Θ) for the flaw from 0 is so much larger than that for the other points that the flaw can be identified.

Figure 13A:
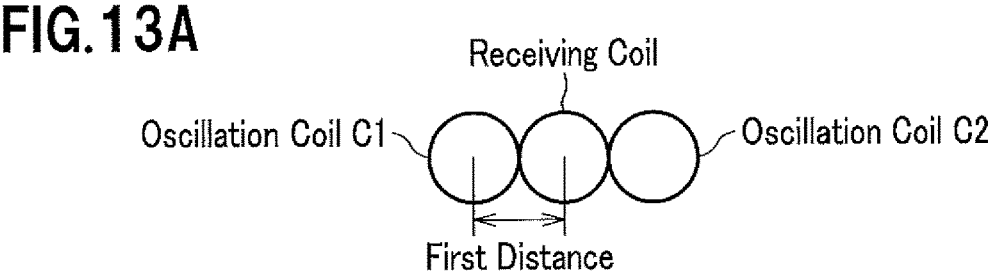
FIG. 13A is a schematic figure of a sensor section that has a smaller distance between coils to detect a flaw on a surface of the railway rail.
Figure 13B:
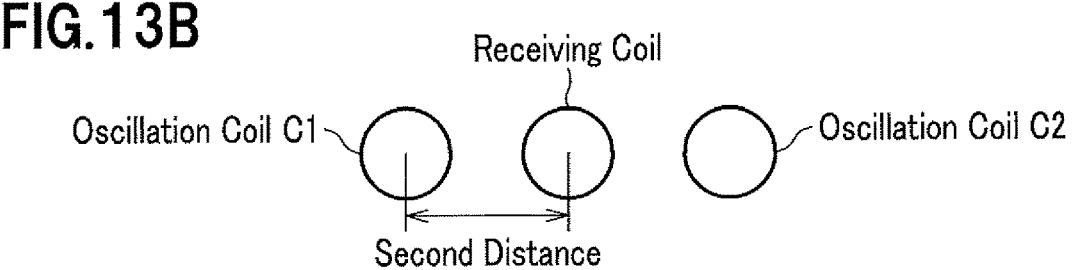
FIG. 13B is a schematic figure of a sensor section that has a larger distance between coils to detect a flaw in the railway rail.

Next, referring to FIGS. 13A, 13B, a relation between a distance between coils and a depth position of the flaw to be detected is explained. The distance between coils indicates a distance from the center of the oscillation coil C1, C2 (or the oscillation coil C2) to the center of the receiving coil.

As shown in FIG. 13A, when the sensor section is intended to detect a flaw on a surface of the rail, the sensor section has a first distance corresponding to the distance between coils. This first distance should depend on a distance between the sensor section and the railway rail PR, a material of which the railway rail PR is made, a cross section shape of the railway rail PR and the like, and can be determined through experiments.

As shown in FIG. 13B, when the sensor section is intended to detect a flaw in the rail, the sensor section has a second distance corresponding to the distance between coils that is larger than the first distance. This second distance can also be determined through experiments.

As has been explained, using different sensor sections whose distances between coils differ from one another enables detecting flaws on the surface of and in the rail and determining whether the detected flaw is on the rail or in the rail.

Figure 14:
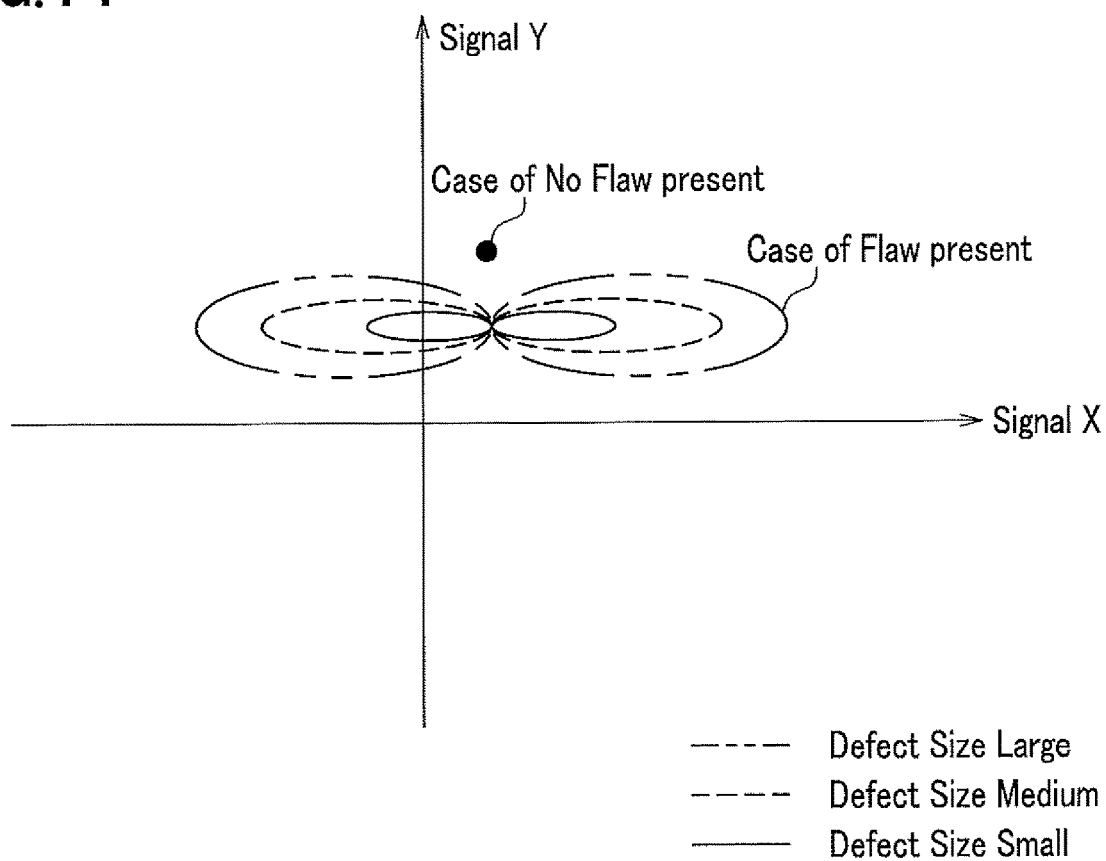
FIG. 14 shows a track of the check data having a cosine component and a sine component plotted on a coordinate plane.

Next, referring to FIG. 14, indications to distinguish the size of a flaw is explained. In FIG. 14 are drawn several tracks based on the signal X and the signal Y on the X-Y coordinate plane. If there is no flaw detected, the track is a point. If there is a flaw detected, the track is, for example, in the shape of a letter "8". Since the larger the track in the shape of a letter "8", the larger the flaw size, it is possible for those who look at the track to recognize the flaw size.

As explained above, the flaw detection device 2 (2a, 2b) utilizes the sensor section 21 inclusive of the oscillation coil C1, the receiving coil and the oscillation coil C2 which are arranged in this order on a plane opposite the rail to be checked, generates from the oscillation coils C1, C2 alternating current magnetic fields whose directions are opposite to each other and is capable of detecting a defect on and in the rail used for the vehicle with a high SN ratio by outputting the magnetic field waveform as check data from the receiving coil In addition, a portion at which a defect is in a railway rail RR can be determined by the evaluation device 4 performing the check process based on the check data received from the detection device 2.

Moreover, other configurations and effects of the present embodiment have been explained.

The explanation on the present embodiment is finished and the scope of the present embodiment is not limited to what have been explained.

For example, the diagonal angle of the sensor section 21c relative to the longitudinal direction of the railway rail RR, which is shown in FIG. 8, may be 30 degrees or other degrees instead of 45 degrees. This applies to the sensor section 21d in FIGS. 8A, 8B.

Furthermore, the specific configuration of the present invention may be altered within the scope of the present invention.

EXPLANATION OF SIGNS

1, 1a Rail Check System
2, 2a, 2b Detection Device (Rail Check Device)
3 Processing Device
4 Evaluation Device
21, 21a, 21b, 21c, 21d Sensor Section
22 Amplification/Filtering Section
31 Amplification Section
32 Digital/Analogue Conversion section
33 Oscillation Section
34 Signal Detection Section
35 Analogue/Digital Section
36 Memory Section
37 Data Communication Section
38 Power Source
41 Data Input Section
42 Control Section
43 Data Processing Section
44 Output Process Section
45 Operation Input Section
46 Display Section
47 Storage Section
211 Oscillation Coil C1, C2
212 Receiving Coil
M Checked Object
RR Railway Rail

The invention claimed is:

1. A rail check system for generating check data for a defect of a rail for vehicles, the rail check system comprising:
    a first oscillation coil and a second oscillation coil which are disposed to face opposite a top portion of the rail, that is a checked object, with center coil axes of the first and second oscillation coils being perpendicular to the top portion of the rail and aligned in a rail longitudinal direction, and configured to generate magnetic fields whose directions are opposite to each other;
    a receiving coil which is disposed between the first oscillation coil and the second oscillation coil and configured to output a magnetic field waveform as the check data based on magnetic field lines leaking from the first oscillation coil and the second oscillation coil and passing through the rail; and
    a rail evaluation device configured to perform a rail check process to determine a defective point of the rail at which there is the defect based on the check data received from the rail check device,
    wherein the rail evaluation device is configured to obtain a first waveform of a cosine component of the magnetic field waveform as the check data outputted from the receiving coil based on the magnetic field lines leaking from the first oscillation coil and the second oscillation coil and passing through the rail, the first waveform being in synchronization with alternate current magnetic fields outputted from the first and second oscillation coils, obtain a second waveform of a sine component of the magnetic field waveform, the second waveform having a phase shifted 90° from the alternate current magnetic fields, compare the first waveform of the cosine component with a third waveform of a square root of a summation of the cosine component of the check data that is squared and a sine component of the check data this squared, and determine the defective point of the rail at a point of the rail at which the first waveform and the third waveform are different from each other.

2. The rail check system according to claim 1, further comprising:
a plurality of sensor sections including at least a first sensor section disposed in parallel with the rail longitudinal direction and which includes the first oscillation coil, the second oscillation coil and the receiving con, a second sensor section disposed orthogonal to the rail longitudinal direction, and a third sensor section disposed in a diagonal direction relative to the rail.

3. The rail system according to claim 1,
wherein the first oscillation coil and the second oscillation coil have a size equal to or larger than a width of the rail, and
wherein the receiving coil is configured by plural receiving coils which are disposed between the first oscillation coil and the second oscillation coil and aligned in a rail width direction, each of the receiving coils being configured to output a magnetic field waveform as the check data.

4. The rail check system according to claim 1,
wherein the rail evaluation device is configured to determine a position of a rail joint in the rail longitudinal direction based on the check data and determine the defective point of the rail in the rail longitudinal direction relative to the position of the rail joint in the rail longitudinal direction.

5. A rail check system for generating check data for a defect of a rail for vehicles, the rail check system comprising:
a first oscillation coil and a second oscillation coil which are disposed to face opposite a top portion of the rail, that is a checked object, with center coil axes of the first and second oscillation coils being perpendicular to the top portion of the rail and aligned in a rail longitudinal direction, and configured to generate magnetic fields whose directions are opposite to each other;
a receiving coil which is disposed between the first oscillation coil and the second oscillation coil and configured to output a magnetic field waveform as the check data based on magnetic field lines leaking from the first oscillation coil and the second oscillation coil and passing through the rail; and
a rail evaluation device configured to perform a rail check process to determine a defective point of the rail at which there is the defect based on the check data received from the rail check device,
wherein the rail evaluation device is configured to obtain a first waveform of a cosine component of the magnetic field waveform as the check data outputted from the receiving coil based on the magnetic field lines leaking from the first oscillation coil and the second oscillation coil and passing through the rail, the first waveform being in synchronization with alternate current magnetic fields outputted from the first and second oscillation coils, obtain a second waveform of a sine component of the magnetic field waveform, the second waveform having a phase shifted 90° from the alternate current magnetic fields, compare the first waveform of the cosine component with a third waveform of an arctangent of the sine component of the check data divided by the cosine component of the check data, and determine the defective point of the rail at a point of the rail at which the first waveform and the third waveform are different from each other.

6. A rail check system for generating check data for a defect of a rail for vehicles, the rail check system comprising:
a first oscillation coil and a second oscillation coil which are disposed to face opposite a top portion of the rail, that is a checked object, with center coil axes of the first and second oscillation coils being perpendicular to the top portion of the rail and aligned in a rail longitudinal direction, and configured to generate magnetic fields whose directions are opposite to each other;
a receiving coil which is disposed between the first oscillation coil and the second oscillation coil and configured to output a magnetic field waveform as the check data based on magnetic field lines leaking from the first oscillation coil and the second oscillation coil and passing through the rail; and
a rail evaluation device configured to perform a rail check process to determine a defective point of the rail at which there is the defect based on the check data received from the rail check device,
wherein the rail evaluation device displays, based on the check data, a track of the check data on a coordinate plane where an X-axis indicates a cosine component signal of the magnetic field waveform as the check data outputted from the receiving coil based on the magnetic field lines leaking from the first oscillation coil and the second oscillation coil and passing through the rail, the cosine component signal being in synchronization with alternate current magnetic fields outputted from the first and second oscillation coils, and a Y-axis indicates a sine component signal of the magnetic field waveform, the sine component signal having a phase shifted 90° from the alternate current magnetic fields.

7. The rail check system according to claim 5, further comprising:
a plurality of sensor sections including at least a first sensor section disposed in parallel with the rail longitudinal direction and which includes the first oscillation coil, the second oscillation coil and the receiving coil, a second sensor section disposed orthogonal to the rail longitudinal direction, and a third sensor section disposed in a diagonal direction relative to the rail.

8. The rail check system according to claim 5,
wherein the first oscillation coil and the second oscillation coil have a size equal to or larger than a width of the rail, and
wherein the receiving coil is configured by plural receiving coils which are disposed between the first oscillation coil and the second oscillation coil and aligned in a rail width direction, each of the receiving coils being configured to output a magnetic field waveform as the check data.

9. The rail check system according to claim 5,
wherein the rail evaluation device is configured to determine a position of a rail joint in the rail longitudinal direction based on the check data and determine the defective point of the rail in the rail longitudinal direction relative to the position of the rail joint in the rail longitudinal direction.

10. The rail check system according to claim 6, further comprising:
a plurality of sensor sections including at least a first sensor section disposed in parallel with the rail longitudinal direction and which includes the first oscillation coil, the second oscillation coil and the receiving coil, a second sensor section disposed orthogonal to the rail longitudinal direction, and a third sensor section disposed in a diagonal direction relative to the rail.

11. The rail check system according to claim 6,
wherein the first oscillation coil and the second oscillation coil have a size equal to or larger than a width of the rail, and
wherein the receiving coil is configured by plural receiving coils which are disposed between the first oscillation coil and the second oscillation coil and aligned in a rail width direction, each of the receiving coils being configured to output a magnetic field waveform as the check data.

12. The rail check system according to claim 6,
wherein the rail evaluation device is configured to determine a position of a rail joint in the rail longitudinal direction based on the check data and determine the defective point of the rail in the rail longitudinal direction relative to the position of the rail joint in the rail longitudinal direction.

* * * * *